(12) United States Patent
Iyer et al.

(10) Patent No.: US 7,825,272 B2
(45) Date of Patent: Nov. 2, 2010

(54) FLUOROCHEMICAL URETHANE COMPOUNDS HAVING PENDENT SILYL GROUPS

(75) Inventors: Suresh Iyer, Woodbury, MN (US); Oscar S. Benz, Pittsburgh, PA (US); Thomas P. Klun, Lakeland, MN (US); Craig A. Burton, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 11 days.

(21) Appl. No.: 12/445,143

(22) PCT Filed: Dec. 5, 2007

(86) PCT No.: PCT/US2007/086446

§ 371 (c)(1), (2), (4) Date: Apr. 10, 2009

(87) PCT Pub. No.: WO2008/076639

PCT Pub. Date: Jun. 26, 2008

(65) Prior Publication Data

US 2010/0105828 A1    Apr. 29, 2010

Related U.S. Application Data

(60) Provisional application No. 60/871,034, filed on Dec. 20, 2006.

(51) Int. Cl.
*C08L 83/00* (2006.01)

(52) U.S. Cl. .................. 556/400; 556/445; 556/465; 528/34; 525/477; 524/588

(58) Field of Classification Search ................ 524/588
See application file for complete search history.

(56) References Cited

U.S. PATENT DOCUMENTS

| | | | |
|---|---|---|---|
| 3,250,808 A | 5/1966 | Moore, Jr. et al. | |
| 3,493,424 A | 2/1970 | Mohriok et al. | |
| 4,262,072 A | 4/1981 | Wendling et al. | |
| 4,351,736 A | 9/1982 | Steinberger et al. | |
| 4,378,250 A | 3/1983 | Treadway et al. | |
| 4,508,916 A | 4/1985 | Newell et al. | |
| 4,781,844 A | 11/1988 | Kortmann et al. | |
| 5,073,442 A | 12/1991 | Knowlton et al. | |
| 5,314,980 A | 5/1994 | Morrison | |
| 6,361,870 B1 | 3/2002 | Steffl et al. | |
| 6,803,109 B2 | 10/2004 | Qiu et al. | |
| 7,078,454 B2 | 7/2006 | Burleigh et al. | |
| 7,094,829 B2 | 8/2006 | Audenaert et al. | |
| 7,097,910 B2 | 8/2006 | Moore et al. | |
| 7,294,731 B1 | 11/2007 | Flynn et al. | |
| 7,351,471 B2 | 4/2008 | Jing et al. | |
| 7,396,429 B2 | 7/2008 | Beckley et al. | |
| 7,473,734 B2 | 1/2009 | Beckley et al. | |
| 7,533,514 B2 | 5/2009 | Hayes | |
| 7,745,653 B2 * | 6/2010 | Iyer et al. ............ | 556/400 |
| 2003/0225178 A1 * | 12/2003 | Purvis ................. | 522/67 |
| 2004/0147188 A1 | 7/2004 | Johnson et al. | |
| 2005/0048288 A1 | 3/2005 | Flynn et al. | |
| 2005/0054804 A1 | 3/2005 | Dams et al. | |
| 2005/0121644 A1 | 6/2005 | Dams et al. | |
| 2005/0164010 A1 | 7/2005 | Trombetta | |
| 2006/0216500 A1 | 9/2006 | Klun et al. | |
| 2009/0025727 A1 | 1/2009 | Klun et al. | |

FOREIGN PATENT DOCUMENTS

| | | |
|---|---|---|
| DE | 1 004 132 | 3/1957 |
| EP | 0 666 290 A1 | 8/1995 |
| EP | 1 564 233 A1 | 8/2005 |
| WO | WO 2005/113642 A1 | 12/2005 |
| WO | WO 2006/102383 A1 | 9/2006 |
| WO | WO 2008/073689 A1 | 6/2008 |

* cited by examiner

*Primary Examiner*—Marc S Zimmer
*Assistant Examiner*—Lindsay Nelson
(74) *Attorney, Agent, or Firm*—Keat S. Kokko

(57) ABSTRACT

Fluorochemical urethane compounds and coating compositions derived therefrom are described. The compounds and compositions may be used in treating substrates, in particular substrates having a hard surface such as ceramics or glass, to render them water, oil, stain, and soil repellent.

19 Claims, No Drawings

FLUOROCHEMICAL URETHANE COMPOUNDS HAVING PENDENT SILYL GROUPS

CROSS REFERENCE TO RELATED APPLICATIONS

This application is a national stage filing under 35 U.S.C. 371 of PCT/US2007/086446, filed Dec. 5, 2007, which claims priority to Provisional Application No. 60/871,034, filed Dec. 20, 2006, the disclosure of which is incorporated by reference in its/their entirety herein.

FIELD OF THE INVENTION

The present invention relates to fluorochemical urethane compounds and coating compositions derived therefrom, which may be used in treating substrates, in particular substrates having a hard surface such as ceramics or glass, to render them water, oil, stain, and soil repellent.

BACKGROUND

Although many fluorinated compositions are known in the art for treating substrates to render them oil and water repellent, there continues to be a desire to provide further improved compositions for the treatment of substrates, in particular substrates having a hard surface such as ceramics, glass and stone, in order to render them water-repellent, oil-repellent, and easy to clean There is also a need for treating glass and plastic as a hard surface, particularly in the optical field, in order to render them stain, dirt and dust resistant. Desirably, such compositions and methods employing them can yield coatings that have improved properties. In particular, it would be desirable to improve the durability of the coating, including an improved abrasion resistance of the coating. Furthermore, improving the ease of cleaning of such substrates while using less detergents, water or manual labor, is not only a desire by the end consumer, but has also a positive impact on the environment. Also, it is desired that the coatings show particularly good chemical and solvent resistance. The compositions should be conveniently be applied in an easy and safe way and are compatible with existing manufacturing methods. Preferably, the compositions will fit easily into the manufacturing processes that are practiced to produce the substrates to be treated.

SUMMARY

The present invention provides fluorochemical urethane compounds of the formula

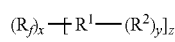

(I)

wherein $R_f$ is a fluorine-containing group, comprising a perfluoroalkyl group, perfluorooxyalkyl group, perfluoroalkylene group and/or a perfluorooxyalkylene group,
$R^1$ is the residue of a polyisocyanate, having a valence of x+y,
$R^2$ is a silane-containing moiety derived from the Michael reaction between an acryloyl group and an aminosilane,
x and y are each independently at least 1, and z is 1 or 2.

In one aspect, this invention relates to chemical compositions comprising one or more compounds (where z is 1) or oligomers (where z is 2) and mixtures thereof having at least one fluorine-containing group and at least one silane-containing moiety derived from the Michael reaction between a nucleophilic acryloyl compound (such as an acrylated polyol having at least one isocyanate-reactive hydroxy group) and an aminosilane.

As used herein, the term "oligomer" means a polymer molecule consisting of only a few, i.e. up to an average of 10, but preferably up to an average of 5, repeating (polymerized) or repeatable units. Each repeating unit comprises a residue of a polyisocyanate that is derived from the reaction of at least one nucleophilic, fluorine-containing compound, aminosilane and polyisocyanate, wherein the fluorine-containing moiety is selected from the group consisting of perfluoroalkyl, perfluoroalkylene, perfluorooxyalkyl, and perfluorooxyalkylene. The oligomer may be terminated with one or more perfluoroalkyl groups, one or more perfluorooxyalkyl groups, and/or one of more silyl groups.

These compounds or oligomers may comprise the Michael reaction product of an aminosilane with a fluorine-containing urethane compound having pendent acryloyl groups; said urethane compound comprising the reaction product of a polyisocyanate, a nucleophilic fluorochemical compound having one or two nucleophilic, isocyanate-reactive functional groups, and a nucleophilic acryloyl compound. In another embodiment, the compounds may comprise the Michael reaction product of an aminosilane with a nucleophilic acryloyl compound, and subsequent reaction product with the polyisocyanate and the fluorine-containing nucleophilic compound.

Unless otherwise stated, the following terms used in the specification and claims have the meanings given below:

"Alkyl" means a linear or branched, cyclic or acylic, saturated monovalent hydrocarbon radical having from one to about twelve carbon atoms, e.g., methyl, ethyl, 1-propyl, 2-propyl, pentyl, and the like.

"Acryloyl" means an acrylate, thioacrylate or acrylamide.

"Alkylene" means a linear saturated divalent hydrocarbon radical having from one to about twelve carbon atoms or a branched saturated divalent hydrocarbon radical having from three to about twelve carbon atoms, e.g., methylene, ethylene, propylene, 2-methylpropylene, pentylene, hexylene, and the like.

"Alkoxy" means an alkyl having a terminal oxygen atom, e.g. $CH_3$—O—, $C_2H_5$—O—, and the like.

"Aralkylene" means an alkylene radical defined above with an aromatic group attached to the alkylene radical, e.g., benzyl, 1-naphthylethyl, and the like.

"Cured chemical composition" means that the chemical composition is dried or solvent has evaporated from the chemical composition from ambient temperature or higher until dryness. The composition may further be crosslinked as result of siloxane bonds formed between the urethane compounds.

"Nucleophilic fluorine-containing compound" means a compound having one or two nucleophilic, isocyanate-reactive functional group, such as a hydroxyl group or an amine group, and a perfluoroalkyl, perfluoroalkylene, perfluorooxyalkyl or perfluorooxyalkylene group, e.g. $CF_9SO_2N(CH_3)CH_2CH_2OH$, $C_4F_9CH_2CH_2OH$, $C_2F_5O(C_2F_4O)_3CF_2CONHC_2H_4OH$, c-$C_6F_{11}CH_2OH$, and the like.

"Fluorochemical urethane compounds" refers to compounds of Formula I, and will include those having urethane linkages per se, or alternatively urea and/or thiourea linkages.

"Hard substrate" means any rigid material that maintains its shape, e.g., glass, ceramic, concrete, natural stone, wood, metals, plastics, and the like.

"Oxyalkoxy" has essentially the meaning given above for alkoxy except that one or more oxygen atoms may be present in the alkyl chain and the total number of carbon atoms present may be up to 50, e.g. $CH_3CH_2OCH_2CH_2O$—, $C_4H_9OCH_2CH_2OCH_2CH_2O$—, $CH_3O(CH_2CH_2O)_{1-100}H$, and the like.

"Oxyalkyl" has essentially the meaning given above for alkyl except that one or more oxygen heteroatoms may be present in the alkyl chain, these heteroatoms being separated from each other by at least one carbon, e.g., $CH_3CH_2OCH_2CH_2$—, $CH_3CH_2OCH_2CH_2OCH(CH_3)CH_2$—, $C_4F_9CH_2OCH_2CH_2$—, and the like.

"Oxyalkylene" has essentially the meaning given above for alkylene except that one or more oxygen heteroatoms may be present in the alkylene chain, these heteroatoms being separated from each other by at least one carbon, e.g., —$CH_2OCH_2O$—, —$CH_2CH_2OCH_2CH_2$—, —$CH_2CH_2OCH_2CH_2CH_2$—, and the like.

"Halo" means fluoro, chloro, bromo, or iodo, preferably fluoro and chloro.

"Perfluoroalkyl" has essentially the meaning given above for "alkyl" except that all or essentially all of the hydrogen atoms of the alkyl radical are replaced by fluorine atoms and the number of carbon atoms is from 1 to about 12, e.g. perfluoropropyl, perfluorobutyl, perfluorooctyl, and the like.

"Perfluoroalkylene" has essentially the meaning given above for "alkylene" except that all or essentially all of the hydrogen atoms of the alkylene radical are replaced by fluorine atoms, e.g., perfluoropropylene, perfluorobutylene, perfluorooctylene, and the like.

"Perfluorooxyalkyl" has essentially the meaning given above for "oxyalkyl" except that all or essentially all of the hydrogen atoms of the oxyalkyl radical are replaced by fluorine atoms and the number of carbon atoms is from 3 to about 100, e.g. $CF_3CF_2OCF_2CF_2$—, $CF_3CF_2O(CF_2CF_2O)_3CF_2CF_2$—, $C_3F_7O(CF(CF_3)CF_2O)_sCF(CF_3)CF_2$—, where s is (for example) from about 1 to about 50, and the like.

"Perfluorooxyalkylene" has essentially the meaning given above for "oxyalkylene" except that all or essentially all of the hydrogen atoms of the oxyalkylene radical are replaced by fluorine atoms, and the number of carbon atoms is from 3 to about 100, e.g., —$CF_2OCF_2$—, or —$[CF_2—CF_2O]_r$—$[CF(CF_3)—CF_2—O]_s$—; wherein r and s are (for example) integers of 1 to 50.

"Perfluorinated group" means an organic group wherein all or essentially all of the carbon bonded hydrogen atoms are replaced with fluorine atoms, e.g. perfluoroalkyl, perfluorooxyalkyl, and the like.

"Polyfunctional isocyanate compound" or "polyisocyanate" means a compound containing an average of greater than one, preferably two or more isocyanate groups, —NCO, attached to a multivalent organic group, e.g. hexamethylene diisocyanate, the biuret and isocyanurate of hexamethylene diisocyanate, and the like.

"Nucleophilic acryloyl compound" means an organic compound with at least one primary or secondary nucleophilic, isocyanate-reactive groups per molecule, and at least one acryloyl group, including acrylate and acrylamide groups.

"Michael addition" refers to an addition reaction wherein an aminosilane undergoes 1,4 addition to an acryloyl group.

DETAILED DESCRIPTION

The present invention provides fluorochemical urethane compounds of formula, described supra.

(I)

wherein $R_f$ is a fluorine-containing group, comprising a perfluoroalkyl group, perfluorooxyalkyl group, perfluoroalkylene group and/or a perfluorooxyalkylene group, $R^1$ is the residue of a polyisocyanate, having a valence of x+y, $R^2$ is a silane-containing moiety derived from the Michael reaction between an acryloyl group and an aminosilane, x and y are each independently at least 1, and z is 1 or 2

With respect to Formula I, $R^2$ is derived by Michael addition of an aminosilane to an acryloyl group, as in the following formula:

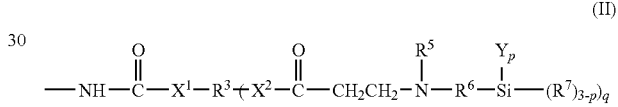

(II)

wherein $X^1$ is —O— or —S—, $X^2$ is —O—, —S— or —$NR^4$—, where $R^4$ is H or $C_1$-$C_4$ alkyl, $R^3$ is a polyvalent alkylene or arylene groups, or combinations thereof, said alkylene groups optionally containing one or more catenary oxygen atoms;

$R^5$ is $C_1$-$C_4$ alkyl, or —$R^6$—$Si(Y_p)(R^7)_{3-p}$;

$R^6$ is a divalent alkylene group, said alkylene groups optionally containing one or more catenary oxygen atoms;

Y is a hydrolysable group, $R^7$ is a monovalent alkyl or aryl group, p is 1, 2 or 3, preferably 3, and q is 1 to 5, preferably 2 to 5.

Although the inventors do not wish to be bound by theory, compounds of the above Formula I are believed to undergo a condensation reaction with the substrate surface to form a siloxane layer via hydrolysis or displacement of the hydrolysable "Y" groups of Formula II. In this context, "siloxane" refers to —Si—O—Si— bonds to which are attached to compounds of Formula I. In the presence of water, the "Y" groups will undergo hydrolysis to "Si—OH" groups, and further condensation to siloxanes.

A coating prepared from the coating composition that includes compounds of Formula I includes the compounds per se, as well as siloxane derivatives resulting from bonding to the surface of a preselected substrate and intermolecular crosslinking by siloxane formation. The coatings can also include unreacted or uncondensed "Si—Y" groups. The composition may further contain non-silane materials such as oligomeric perfluorooxyalkyl monohydrides, starting materials and perfluorooxyalkyl alcohols and esters.

In one embodiment, the invention provides a coating composition comprising the compound of Formula I, a solvent, and optionally water and an acid. In another embodiment, the coating composition comprises an aqueous suspension or dispersion of the compounds. To achieve good durability for many substrates, such as ceramics, the compositions of the present invention preferably include water. Thus the present invention provides a method of coating comprising the steps of providing contacting a substrate with a coating composition comprising the compound of Formula I and a solvent. The coating composition may further comprise water and an acid. In one embodiment the method comprises contacting a substrate with a coating composition comprising the silane of Formula I and a solvent, and subsequently contacting the substrate with an aqueous acid.

Polyisocyanate compounds useful in preparing the fluorochemical compounds of the present invention comprise isocyanate radicals attached to the multivalent organic group ($R^1$) that can comprise a multivalent aliphatic, alicyclic, or aromatic moiety; or a multivalent aliphatic, alicyclic or aromatic moiety attached to a biuret, an isocyanurate, or a uretdione, or mixtures thereof. Preferred polyfunctional isocyanate compounds contain an average of at least two isocyanate (—NCO) radicals. Compounds containing at least two —NCO radicals are preferably comprised of di- or trivalent aliphatic, alicyclic, araliphatic, or aromatic groups to which the —NCO radicals are attached. Aliphatic di- or trivalent groups are preferred.

Representative examples of suitable polyisocyanate compounds include isocyanate functional derivatives of the polyisocyanate compounds as defined herein. Examples of derivatives include, but are not limited to, those selected from the group consisting of ureas, biurets, allophanates, dimers and trimers (such as uretdiones and isocyanurates) of isocyanate compounds, and mixtures thereof. Any suitable organic polyisocyanate, such as an aliphatic, alicyclic, araliphatic, or aromatic polyisocyanate, may be used either singly or in mixtures of two or more.

The aliphatic polyisocyanate compounds generally provide better light stability than the aromatic compounds. Aromatic polyisocyanate compounds, on the other hand, are generally more economical and reactive toward nucleophiles than are aliphatic polyisocyanate compounds. Suitable aromatic polyisocyanate compounds include, but are not limited to, those selected from the group consisting of 2,4-toluene diisocyanate (TDI), 2,6-toluene diisocyanate, an adduct of TDI with trimethylolpropane (available as Desmodur™ CB from Bayer Corporation, Pittsburgh, Pa.), the isocyanurate trimer of TDI (available as Desmodur™ IL from Bayer Corporation, Pittsburgh, Pa.), diphenylmethane 4,4'-diisocyanate (MDI), diphenylmethane 2,4'-diisocyanate, 1,5-diisocyanato-naphthalene, 1,4-phenylene diisocyanate, 1,3-phenylene diisocyanate, 1-methoxy-2,4-phenylene diisocyanate, 1-chlorophenyl-2,4-diisocyanate, and mixtures thereof.

Examples of useful alicyclic polyisocyanate compounds include, but are not limited to, those selected from the group consisting of dicyclohexylmethane diisocyanate ($H_{12}$ MDI, commercially available as Desmodur™ available from Bayer Corporation, Pittsburgh, Pa.), 4,4'-isopropyl-bis(cyclohexylisocyanate), isophorone diisocyanate (IPDI), cyclobutane-1,3-diisocyanate, cyclohexane 1,3-diisocyanate, cyclohexane 1,4-diisocyanate (CHDI), 1,4-cyclohexanebis(methylene isocyanate) (BDI), dimmer acid diisocyanate (available from Bayer), 1,3-bis(isocyanatomethyl)cyclohexane ($H_6XDI$), 3-isocyanatomethyl-3,5,5-trimethylcyclohexyl isocyanate, and mixtures thereof.

Examples of useful aliphatic polyisocyanate compounds include, but are not limited to, those selected from the group consisting of tetramethylene 1,4-diisocyanate, hexamethylene 1,4-diisocyanate, hexamethylene 1,6-diisocyanate (HDI), octamethylene 1,8-diisocyanate, 1,12-diisocyanatododecane, 2,2,4-trimethyl-hexamethylene diisocyanate (TMDI), 2-methyl-1,5-pentamethylene diisocyanate, dimer diisocyanate, the urea of hexamethylene diisocyanate, the biuret of hexamethylene 1,6-diisocyanate (HDI) (Desmodur™ N-100 and N-3200 from Bayer Corporation, Pittsburgh, Pa.), the isocyanurate of HDI (available as Desmodur™ N-3300 and Desmodur™ N-3600 from Bayer Corporation, Pittsburgh, Pa.), a blend of the isocyanurate of HDI and the uretdione of HDI (available as Desmodure™ N-3400 available from Bayer Corporation, Pittsburgh, Pa.), and mixtures thereof.

Examples of useful araliphatic polyisocyanates include, but are not limited to, those selected from the group consisting of m-tetramethyl xylylene diisocyanate (m-TMXDI), p-tetramethyl xylylene diisocyanate (p-TMXDI), 1,4-xylylene diisocyanate (XDI), 1,3-xylylene diisocyanate, p-(1-isocyanatoethyl)phenyl isocyanate, m-(3-isocyanatobutyl)phenyl isocyanate, 4-(2-isocyanatocyclohexyl-methyl)phenyl isocyanate, and mixtures thereof.

Preferred polyisocyanates, in general, include those selected from the group consisting of tetramethylene 1,4-diisocyanate, hexamethylene 1,4-diisocyanate, hexamethylene 1,6-diisocyanate (HDI), octamethylene 1,8-diisocyanate, 1,12-diisocyanatododecane, and the like, and mixtures thereof. Fluorochemical compositions of the present invention comprising compounds or oligomers made with preferred polyisocyanates impart both high water and hexadecane receding dynamic contact angles. High water receding dynamic contact angle together with high hexadecane receding dynamic contact angle is typically predictive of good water-repellency and oil-repellency properties.

The fluorochemical urethane comprises, in part, the reaction product of a fluorochemical compound having a mono- or difunctional perfluorinated group, and at least one nucleophilic, isocyanate-reactive functional group. Such compounds include those of the formula:

$$R_f^1\text{-}[Q(X^2H)_y]_z, \quad (III)$$

where $R_f^1$ is a monovalent perfluoroalkyl or a perfluorooxyalkyl group (where z is 1), or a divalent perfluoroalkylene or a perfluorooxyalkylene group (where z is 2), Q is a covalent bond, or a polyvalent alkylene group of valency z, said alkylene optionally containing one or more catenary (in-chain) nitrogen or oxygen atoms, and optionally containing one or more sulfonamide, carboxamido, or carboxy functional groups;

$X^2$ is —O—, —$NR^4$— or —S—, where $R^4$ is H or $C_1$-$C_4$ alkyl, y is 1 or 2, and z is 1 or 2.

With respect to Formulas I and III, the reaction between the nucleophilic fluorochemical compound (III) and an isocyanate group of a polyisocyanate produces a urea- or urethane-linked fluorine-containing group. Thus $R_f$ of Formula I is of the Formula IV.

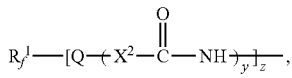 (IV)

where $R_f^1$ is a monovalent perfluoroalkyl or a perfluorooxyalkyl group (where z is 1), or a divalent perfluoroalkylene or a perfluorooxyalkylene group (where z is 2), Q is a covalent bond, or a polyvalent alkylene group of valency z, said alkylene optionally containing one or more catenary (in-chain) nitrogen or oxygen atoms, and optionally containing one or more sulfonamide, carboxamido, or carboxy functional groups;

$X^2$ is —O—, —$NR^4$— or —S—, where $R^4$ is H or $C_1$-$C_4$ alkyl, y is 1 or 2, and z is 1 or 2.

The $R_f^1$ groups of Formula III and IV can contain straight chain, branched chain, or cyclic fluorochemical groups or any combination thereof. The $R_f^1$ groups can be mono- or divalent, and can optionally contain one or more catenary oxygen atoms in the carbon-carbon chain so as to form a carbon-oxygen-carbon chain (i.e. a perfluorooxyalkylene group). Fully-fluorinated groups are generally preferred, but hydrogen or other halo atoms can also be present as substituents, provided that no more than one atom of either is present for every two carbon atoms.

It is additionally preferred that any $R_f^1$ group contain at least about 40% fluorine by weight, more preferably at least about 50% fluorine by weight. The terminal portion of the monovalent $R_f^1$ group is generally fully-fluorinated, preferably containing at least three fluorine atoms, e.g., $CF_3$—, $CF_3CF_2$—, $CF_3CF_2CF_2$—, $(CF_3)_2N$—, $(CF_3)_2CF$—, $SF_5CF_2$—. In certain embodiments, monovalent perfluoroalkyl groups (i.e., those of the formula $C_nF_{2n+1}$—) or divalent perfluoroalkylene groups (i.e., those of the formula —$C_nF_2$—) wherein n is 2 to 12 inclusive are the preferred $R_f^1$ groups, with n=3 to 5 being more preferred and with n=4 being the most preferred.

Useful perfluorooxyalkyl and perfluorooxyalkylene $R_f^1$ groups correspond to the formula:

 (V)

wherein

W is F for monovalent perfluorooxyalkyl, and an open valence ("-") for divalent perfluorooxyalkylene $R_f^3$ represents a perfluoroalkylene group, $R_f^4$ represents a perfluoroalkyleneoxy group consisting of perfluoroalkyleneoxy groups having 1, 2, 3 or 4 carbon atoms or a mixture of such perfluoroalkyleneoxy groups, $R_f^5$ represents a perfluoroalkylene group and q is 0 or 1. The perfluoroalkylene groups $R_f^3$ and $R_f^5$ in formula (IV) may be linear or branched and may comprise 1 to 10 carbon atoms, preferably 1 to 6 carbon atoms. A typical monovalent perfluoroalkyl group is $CF_3$—$CF_2$—$CF_2$— and a typical divalent perfluoroalkylene is —$CF_2$—$CF_2$—$CF_2$—, —$CF_2$— or —$CF(CF_3)CF_2$—. Examples of perfluoroalkyleneoxy groups $R_f^4$ include: —$CF_2$—$CF_2$—O—, —$CF(CF_3)$—$CF_2$—O—, —$CF_2$—$CF(CF_3)$—O—, —$CF_2$—$CF_2$—$CF_2$—O—, —$CF_2$—O—, —$CF(CF_3)$—O—, and —$CF_2$—$CF_2$—$CF_2$—$CF_2$—O—.

The perfluoroalkyleneoxy group $R_f^4$ may be comprised of the same perfluorooxyalkylene units or of a mixture of different perfluorooxyalkylene units. When the perfluorooxyalkylene group is composed of different perfluoroalkylene oxy units, they can be present in a random configuration, alternating configuration or they can be present as blocks. Typical examples of perfluorinated poly(oxyalkylene) groups include: —$[CF_2$—$CF_2$—O$]_r$—; —$[CF(CF_3)$—$CF_2$—O$]_s$—; —$[CF_2CF_2$—O$]_r$—$[CF_2O]_t$—, —$[CF_2CF_2CF_2CF_2$—O$]_u$ and —$[CF_2$—$CF_2$—O$]_r$—$[CF(CF_3)$—$CF_2$—O$]_s$—; wherein each of r, s, t and u each are integers of 1 to 50, preferably 2 to 25. A preferred perfluorooxyalkyl group that corresponds to formula (V) is $CF_3$—$CF_2$—$CF_2$—O—$[CF(CF_3)$—$CF_2O]_s$—$CF(CF_3)CF_2$— wherein s is an integer of 2 to 25.

Perfluorooxyalkyl and perfluoroxyalkylene compounds can be obtained by oligomerization of hexafluoropropylene oxide that results in a terminal carbonyl fluoride group. This carbonyl fluoride may be converted into an acid, ester or alcohol by reactions well known to those skilled in the art. The carbonyl fluoride or acid, ester or alcohol derived therefrom may then be reacted further to introduce the desired isocyanate reactive groups according to known procedures.

With respect to Formula I, where y or z is 1, fluorochemical monofunctional compounds, preferably monoalcohols and monoamines are contemplated. Representative examples of useful fluorochemical monofunctional compounds include the following: $CF_3(CF_2)_3SO_2N(CH_3)CH_2CH_2OH$, $CF_3(CF_2)_3SO_2N(CH_3)CH(CH_3)CH_2OH$, $CF_3(CF_2)_3SO_2N(CH_3)CH_2CH(CH_3)NH_2$, $CF_3(CF_2)_3SO_2N(CH_2CH_3)CH_2CH_2SH$, $CF_3(CF_2)_3SO_2N(CH_3)CH_2CH_2SCH_2CH_2OH$, $C_6F_{13}SO_2N(CH)(CH_2)_4OH$, $CF_3(CF_2)_7SO_2N(H)(CH_2)_3OH$, $C_3F_7SO_2N(CH_3)CH_2CH_2OH$, $CF_3(CF_2)_4SO_2N(CH_3)(CH_2)_4NH_2$, $C_4F_9SO_2N(CH_3)(CH_2)_{11}OH$, $CF_3(CF_2)_5SO_2N(CH_2CH_3)CH_2CH_2OH$, $CF_3(CF_2)_5SO_2N(C_2H_5)(CH_2)_6OH$, $CF_3(CF_2)_2SO_2N(C_2H_5)(CH_2)_4OH$, $CF_3(CF_2)_3SO_2N(C_3H_7)CH_2OCH_2CH_2CH_2OH$, $CF_3(CF_2)_4SO_2N(CH_2CH_2CH_3)CH_2CH_2OH$, $CF_3(CF_2)_4SO_2N(CH_2CH_2CH_3)CH_2CH_2NHCH_3$, $CF_3(CF_2)_3SO_2N(C_4H_9)CH_2CH_2NH_2$, $CF_3(CF_2)_3SO_2N(C_4H_9)(CH_2)_4SH$, $CF_3(CF_2)_3CH_2CH_2OH$, $C_4F_9OC_2F_4OCF_2CH_2OCH_2CH_2OH$; $n$-$C_6F_{13}CF(CF_3)CON(H)CH_2CH_2OH$; $C_6F_{13}CF(CF_3)CO_2C_2H_4CH(CH_3)OH$; $C_3F_7CON(H)CH_2CH_2OH$; $C_3F_7O(CF(CF_3)CF_2O)_{1-36}CF(CF_3)CH_2OH$; and $C_3F_7O(CF(CF_3)CF_2O)_{1-36}CF(CF_3)C(O)N(H)CH_2CH_2OH$ and the like, and mixtures thereof. If desired, other isocyanate-reactive functional groups may be used in place of those depicted.

With respect to Formula I, where y or z is 2, fluorinated polyols are preferred. Representative examples of suitable fluorinated polyols include $R_f^1SO_2N(CH_2CH_2OH)_2$ such as N-bis(2-hydroxyethyl)perfluorobutylsulfonamide; $R_f^1OC_6H_4SO_2N(CH_2CH_2OH)_2$; $R_f^1SO_2N(R')CH_2CH(OH)CH_2OH$ such as $C_6F_{13}SO_2N(C_3H_7)CH_2CH(OH)CH_2OH$; $R_f^1CH_2CON(CH_2CH_2OH)_2$; $CF_3CF_2(OCF_2CF_2)_3OCF_2CON(CH_3)CH_2CH(OH)CH_2OH$; $R_f^1OCH_2CH(OH)CH_2OH$ such as $C_4F_9OCH_2CH(OH)CH_2OH$; $R_f^1CH_2CH_2SC_3H_6OCH_2CH(OH)CH_2OH$; $R_f^1CH_2CH_2SC_3H_6CH(CH_2OH)_2$; $R_f^1CH_2CH_2SCH_2CH(OH)CH_2OH$; $R_f^1CH_2CH_2SCH(CH_2OH)CH_2CH_2OH$; $R_f^1CH_2CH_2CH_2SCH_2CH(OH)CH_2OH$ such as $C_5F_{11}(CH_2)_3SCH_2CH(OH)CH_2OH$; $R_f^1CH_2CH_2CH_2OCH_2CH(OH)CH_2OH$ such as $C_5F_{11}(CH_2)_3OCH_2CH(OH)CH_2OH$; $R_f^1CH_2CH_2CH_2OC_2H_4OCH_2CH(OH)CH_2OH$; $R_f^1CH_2CH_2(CH_3)OCH_2CH(OH)CH_2OH$; $R_f^1(CH_2)_4SC_3H_6CH(CH_2OH)CH_2OH$; $R_f^1(CH_2)_4SCH_2CH(CH_2OH)_2$; $R_f^1(CH_2)_4$ $SC_3H_6OCH_2CH(OH)CH_2OH$; $R_f^1CH_2CH(C_4H_9)SCH_2CH(OH)CH_2OH$; $R_f^1CH_2OCH_2CH(OH)CH_2OH$; $R_f^1CH_2CH(OH)CH_2SCH_2CH_2OH$; $R_f^1CH_2CH(OH)

CH₂SCH₂CH₂OH; R<sub>f</sub>¹CH₂CH(OH)CH₂OCH₂CH₂OH; R<sub>f</sub>¹CH₂CH(OH)CH₂OH; R<sub>f</sub>¹R"SCH(R'"OH)CH(R'"OH)SR"R<sub>f</sub>; (R<sub>f</sub>¹CH₂CH₂SCH₂CH₂SCH₂)₂C(CH₂OH)₂; ((CF₃)₂CFO(CF₂)₂(CH₂)₂SCH₂)₂C(CH₂OH)₂; (R<sub>f</sub>¹R"SCH₂)₂C(CH₂OH)₂; 1,4-bis(1-hydroxy-1,1-dihydro-perfluoroethoxyethoxy)perfluoro-n-butane (HOCH₂CF₂OC₂F₄O(CF₂)₄OC₂F₄OCF₂CH₂OH); 1,4-bis(1-hydroxy-1,1-dihydroperfluoropropoxy)perfluoro-n-butane (HOCH₂CF₂CF₂O(CF₂)₄OCF₂CF₂CH₂OH); fluorinated oxetane polyols made by the ring-opening polymerization of fluorinated oxetane such as Poly-3-Fox™ (available from Omnova Solutions, Inc., Akron Ohio); polyetheralcohols prepared by ring opening addition polymerization of a fluorinated organic group substituted epoxide with a compound containing at least two hydroxyl groups as described in U.S. Pat. No. 4,508,916 (Newell et al); and perfluoropolyether diols such as Fomblin™ ZDOL (HOCH₂CF₂O(CF₂O)₈₋₁₂(CF₂CF₂O)₈₋₁₂CF₂CH₂OH, available from Ausimont); wherein R<sub>f</sub> is a perfluoroalkyl group having 1 to 12 carbon atoms, or a perfluorooxyalkyl group having 3 to about 50 carbon atoms with all perfluorocarbon chains present having 6 or fewer carbon atoms, or mixtures thereof; R' is alkyl of 1 to 4 carbon atoms; R" is branched or straight chain alkylene of 1 to 12 carbon atoms, alkylenethioalkylene of 2 to 12 carbon atoms, alkylene-oxyalkylene of 2 to 12 carbon atoms, or alkylene iminoalkylene of 2 to 12 carbon atoms, where the nitrogen atom contains as a third substituent hydrogen or alkyl of 1 to 6 carbon atoms; and R'" is a straight or branched chain alkylene of 1 to 12 carbon atoms or an alkylene-polyoxyalkylene of formula $C_rH_{2r}(OC_sH_{2s})_t$ where r is 1-12, s is 2-6, and t is 1-40.

Preferred fluorinated polyols include N-bis(2-hydroxyethyl) perfluorobutylsulfonamide; fluorinated oxetane polyols made by the ring-opening polymerization of fluorinated oxetane such as Poly-3-Fox™ (available from Omnova Solutions, Inc., Akron Ohio); polyetheralcohols prepared by ring opening addition polymerization of a fluorinated organic group substituted epoxide with a compound containing at least two hydroxyl groups as described in U.S. Pat. No. 4,508,916 (Newell et al); perfluoropolyether diols such as Fomblin™ ZDOL (HOCH₂CF₂O(CF₂O)₈₋₁₂(CF₂CF₂O)₈₋₁₂CF₂CH₂OH, available from Ausimont); 1,4-bis(1-hydroxy-1,1-dihydroperfluoroethoxyethoxy)perfluoro-n-butane (HOCH₂CF₂OC₂F₄O(CF₂)₄OC₂F₄OCF₂CH₂OH); and 1,4-bis(1-hydroxy-1,1-dihydroperfluoropropoxy)perfluoro-n-butane (HOCH₂CF₂CF₂O(CF₂)₄OCF₂CF₂CH₂OH).

More preferred polyols comprised of at least one fluorine-containing group include N-bis(2-hydroxyethyl)perfluorobutylsulfonamide; 1,4-bis(1-hydroxy-1,1-dihydroperfluoropropoxy)perfluoro-n-butane (HOCH₂CF₂CF₂O(CF₂)₄OCF₂CF₂CH₂OH) and CF₃CF₂CF₂—O—[CF(CF₃)CF₂O]<sub>n</sub>—CF(CF₃)—, wherein n is an integer of 3 to 25. This perfluorinated polyether group can be derived from an oligomerization of hexafluoropropylene oxide. Such perfluorinated polyether groups are preferred in particular because of their benign environmental properties.

The fluorochemical urethane comprises, in part, the reaction product of a nucleophilic acryloyl compound having an isocyanate-reactive, nucleophilic functional group and least one acryloyl group (hereinafter a "nucleophilic acryloyl compound"). The acryloyl moiety may be an acrylate or acrylamide, and the nucleophilic functional group may be an amino or hydroxy group. Preferably, the nucleophilic acryloyl compound is a polyacryl compound having a hydroxyl group and at least two acryloyl groups.

Such compounds include those of the formula:

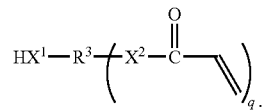

where

X¹ is —O— or —S—, preferably —O—;

X² is —O—, —S— or —NR⁴—, preferably —O—, where R⁴ is H or C₁-C₄ alkyl,

R³ is a polyvalent alkylene or arylene groups, or combinations thereof, said alkylene groups optionally containing one or more catenary oxygen atoms; and q is 1 to 5.

Preferably q is greater than 1. The resulting multiple acryloyl groups allow the addition of multiple silane groups to the urethane compound. The molar ratio of silane groups to —NH—C(O)—X¹— groups may be greater than 1:1, or greater than 2:1. Preferably HX¹— is not directly connected to an aromatic ring, such as with a phenolic compound.

Useful nucleophilic acryloyl compounds include, for example, acrylate compounds selected from the group consisting of (a) monoacryloyl containing compounds such as hydroxyethyl acrylate, glycerol monoacrylate 1,3-butylene glycol monoacrylate, 1,4-butanediol monoacrylate, 1,6-hexanediol monoacrylate, alkoxylated aliphatic monoacrylate, cyclohexane dimethanol monoacrylate, alkoxylated hexanediol monoacrylate, alkoxylated neopentyl glycol monoacrylate, caprolactone modified neopentylglycol hydroxypivalate acrylate, caprolactone modified neopentylglycol hydroxypivalate monoacrylate, diethylene glycol monoacrylate, dipropylene glycol monoacrylate, ethoxylated bisphenol-A monoacrylate, hydroxypivalaldehyde modified trimethylolpropane monoacrylate, neopentyl glycol monoacrylate, propoxylated neopentyl glycol monoacrylate, tetraethylene glycol monoacrylate, tricyclodecanedimethanol monoacrylate, triethylene glycol monoacrylate, tripropylene glycol monoacrylate; (b) multiacryloyl-containing compounds such as glycerol diacrylate, ethoxylated triacrylates (e.g., ethoxylated trimethylolpropane diiacrylate), pentaerythritol triacrylate, propoxylated diacrylates (e.g., propoxylated (3) glyceryl diacrylate, propoxylated (5.5) glyceryl diacrylate, propoxylated (3) trimethylolpropane diacrylate, propoxylated (6) trimethylolpropane diacrylate), trimethylolpropane diacrylate, higher functionality (meth)acryl containing compounds such as di-trimethylolpropane tetraacrylate, and dipentaerythritol pentaacrylate.

Such compounds are widely available from vendors such as, for example, Sartomer Company, Exton, Pa.; UCB Chemicals Corporation, Smyrna, Ga.; and Aldrich Chemical Company, Milwaukee, Wis. Additional useful acrylate materials include dihydroxyhydantoin moiety-containing polyacrylates, for example, as described in U.S. Pat. No. 4,262,072 (Wendling et al.).

With respect to the exemplary nucleophilic acryloyl compounds, it will be understood that the corresponding acrylamides may be used. Further, the indicated hydroxyl groups may be substituted by the corresponding thiol group.

The fluorochemical urethane compounds comprise, in part, the Michael reaction product of an aminosilane with an acryloyl group. The aminosilane may be reacted with the nucleophilic acryloyl compound to form a Michael adduct, which may subsequently be reacted with the polyisocyanate (either before or after functionalization by the nucleophilic fluorochemical compound. Preferably, the nucleophilic acryloyl compound is first reacted with the polyisocyanate (again, before or after reaction with the nucleophilic fluorochemical compound, to form a urethane compound having pendent acryloyl groups, to which is added the aminosilane by Michael addition.

Preferred aminosilanes may be represented by the general formula:

(VII)

wherein $R^5$ is H, $C_1$-$C_4$ alkyl, or —$R^6$—Si($Y_p$)($R^7$)$_{3-p}$;

$R^6$ is a divalent alkylene group, said alkylene groups optionally containing one or more catenary oxygen atoms;

Y is a hydrolysable group, $R^7$ is a monovalent alkyl or aryl group, p is 1, 2 or 3, preferably 3.

It will be understood that in the presence of water, the Y groups may hydrolyzed to —OH groups, leading to reaction with a substrate surface to form siloxane linkages Bonds thus formed, particularly Si—O—Si bonds, are water resistant and can provide enhanced durability of the stain-release properties imparted by the chemical compositions of the present invention With respect to the aminosilanes of Formula VII, it should be noted that primary amines, those where $R^5$ is H, are capable of reacting with two acryloyl groups by Michael addition, which may lead to crosslinking of the fluorochemical urethane compounds of Formula I. Further, primary amines may also compete with the Michael addition of the aminosilane to the acryloyl groups. For these reasons, $R^5$=H is not preferred, although 20 mole percent of such primary aminosilanes may be used.

Some aminosilanes useful in the practice of this invention are described in U.S. Pat. No. 4,378,250 and include aminoethyltriethoxysilane, β-aminoethyltrimethoxysilane, β-aminoethyltriethoxysilane, β-aminoethyltributoxysilane, β-aminoethyltripropoxysilane, α-amino-ethyltrimethoxysilane, α-aminoethyltriethoxysilane, γ-aminopropyltrimethoxysilane, γ-aminopropyltrimethoxysilane, γ-aminopropyltriethoxysilane, γ-aminopropyltributoxysilane, γ-aminopropyltripropoxysilane, β-aminopropyltrimethoxysilane, β-aminopropyltriethoxysilane, β-aminopropyltripropoxysilane, β-aminopropyltributoxysilane, α-aminopropyltrimethoxysilane, α-aminopropyltriethoxysilane, α-aminopropyltributoxysilane, α-aminopropyltripropoxysilane, Minor amounts (<20 mole percent) of catenary nitrogen-containing aminosilanes may also be used, including those described in U.S. Pat. No. 4,378,250. N-(β-aminoethyl)-β-aminoethyltrimethoxysilane, N-(β-aminoethyl)-β-aminoethyltriethoxysilane, N-(β-aminoethyl)-β-aminoethyltripropoxysilane, N-(β-aminoethyl)-α-aminoethyltrimethoxysilane, N-(β-aminoethyl)-α-aminoethyltriethoxysilane, N-(β-aminoethyl)-α-aminoethyltripropoxysilane, N-(β-aminoethyl)-β-aminopropyltrimethoxysilane, N-(β-aminoethyl)-γ-aminopropyltriethoxysilane, N-(β-aminoethyl)-γ-aminopropyltripropoxysilane, N-(β-aminoethyl)-γ-aminopropyltrimethoxysilane, N-(β-aminoethyl)-β-aminopropyltriethoxysilane, N-(β-aminoethyl)-β-aminopropyltripropoxysilane, N-(γ-aminopropyl)-β-aminoethyltrimethoxysilane, N-(γ-aminopropyl)-β-aminoethyltriethoxysilane, N-(γ-aminopropyl)-β-aminoethyltripropoxysilane, N-methylaminopropyltrimethoxysilane, β-aminopropylmethyl diethoxysilane, and γ-diethylene triaminepropyltriethoxysilane.

The fluorochemical compounds can be made by simple blending of the nucleophilic acryloyl compound(s), fluorine-containing nucleophilic compound(s), and the polyisocyanate compound(s), to produce a urethane compound of the formula:

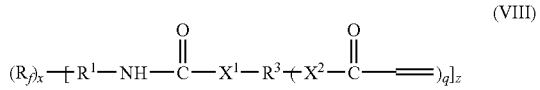

(VIII)

wherein $R_f$ is a fluorine-containing group, comprising a monovalent perfluoroalkyl or a perfluorooxyalkyl group, or a divalent perfluoroalkylene or a perfluorooxyalkylene group, $R^1$ is the residue of a polyisocyanate, $X^1$ is —O— or —S—, $X^2$ is —O—, —S— or —$NR^4$—, where $R^4$ is H or $C_1$-$C_4$ alkyl, $R^3$ is a divalent alkylene or arylene groups, or combinations thereof, said alkylene groups optionally containing one or more catenary oxygen atoms;

x is 1 or 2, z is 1 or 2, and q is 1 to 5.

This is followed by Michael addition of the aminosilanes (VII) to the acryloyl groups. As one skilled in the art would understand, the order of blending or the ordering of the steps is non-limiting and can be modified so as to produce a desired fluorochemical urethane compounds. In a preferred embodiment, the polyisocyanate compound(s), the fluorine-containing nucleophilic compound (III) are first reacted with some portion of the isocyanate groups whereby pendent fluorine-containing groups are thereby bonded to the isocyanate functional urethane compounds. This is followed by reaction with the nucleophilic acryloyl compound(s) with some portion of the remaining isocyanate groups, followed by Michael addition of the aminosilane to the pendent acryloyl groups. Where the nucleophilic fluorochemical compound is an amine, this generally precedes further functionalization by the nucleophilic acryloyl compound, as an amine functional group will compete with Michael addition by the aminosilane.

In general, the reactive components and a solvent are charged to a dry reaction vessel in immediate succession or as pre-made mixtures. When a homogeneous mixture or solution is obtained a catalyst is optionally added, and the reaction mixture is heated at a temperature, and for a time sufficient for the reaction to occur. Progress of the reaction can be determined by monitoring the disappearance of the isocyanate peak in the IR.

The nucleophilic compound $R_f^1$-Q($X^2$H)$_z$ (III), is used in an amount sufficient to react with 5 to 50 mole percent of the available isocyanate functional groups. Preferably, compound III is used to react with 10 to 30 mole percent of the isocyanate groups. The remaining isocyanate groups, about 50 to 95 mole percent, preferably 70 to 90 mole percent is functionalized by the nucleophilic acryloyl compound (VI), followed by Michael addition of the aminosilane (VII), resulting in a urethane compound having both pendent fluorochemical groups and pendent acryloyl groups.

Alternatively, the aminosilane (VII) and the nucleophilic acryloyl compound (VI) may be pre-reacted, and then this Michael adduct of Formula IX is reacted with the remaining isocyanate groups. The fluorochemical urethane, corresponding to Formula I, generally has essentially no remaining isocyanate groups by IR.

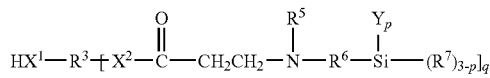

(IX)

Depending on reaction conditions (e.g., reaction temperature and/or polyisocyanate used), a catalyst level of up to about 0.5 percent by weight of the reaction mixture may be used to effect the condensation reactions with the isocyanates, but typically about 0.00005 to about 0.5 percent by weight may be used, 0.02 to 0.1 percent by weight being preferred. In general, if the nucleophilic group is an amine group, a catalyst is not necessary.

Suitable catalysts include, but are not limited to, tertiary amine and tin compounds. Examples of useful tin compounds include tin II and tin IV salts such as stannous octoate, dibutyltin dilaurate, dibutyltin diacetate, dibutyltin di-2-ethylhexanoate, and dibutyltinoxide. Examples of useful tertiary amine compounds include triethylamine, tributylamine, triethylenediamine, tripropylamine, bis(dimethylaminoethyl) ether, morpholine compounds such as ethyl morpholine, and 2,2'-dimorpholinodiethyl ether, 1,4-diazabicyclo[2.2.2]octane (DABCO, Aldrich Chemical Co., Milwaukee, Wis.), and 1,8-diazabicyclo[5.4.0.]undec-7-ene (DBU, Aldrich Chemical Co., Milwaukee, Wis.). Tin compounds are preferred. If an acid catalyst is used, it is preferably removed from the product or neutralized after the reaction. It has been found that the presence of the catalyst may deleteriously affect the contact angle performance.

Although no catalyst is required for the Michael addition of the aminosilanes to the acryloyl groups, suitable catalysts for the Michael reaction is a base of which the conjugated acid preferably has a pKa between 12 and 14. Most preferably used bases are organic. Examples of such bases are 1,4-dihydropyridines, methyl diphenylphosphane, methyl di-p-tolylphosphane, 2-allyl-N-alkyl imidazolines, tetra-t-butylammonium hydroxide, DBU (1,8-diazabicyclo[5.4.0] undec-7-ene) and DBN (1,5-diazabicyclo[4.3.0]non-5-ene), potassium methoxide, sodium methoxide, sodium hydroxide, and the like. A preferred catalyst in connection with this invention is DBU and tetramethylguanidine. The amount of catalyst used in the Michael addition reaction is preferably between 0.05% by weight and 2% by weight more preferably between 0.1% by weight and 1.0% by weight, relative to solids.

Compositions according to the present invention may be coated on a substrate and at least partially cured to provide a coated article. In some embodiments, the polymerized coating may form a protective coating that provides at least one of mar resistance, graffiti resistance, stain resistance, adhesive release, low refractive index, and water repellency. Coated articles according to the present invention include, for example, eyeglass lenses, mirrors, windows, adhesive release liners, and anti-graffiti films.

Suitable substrates include, for example, glass (e.g., windows and optical elements such as, for example, lenses and mirrors), ceramic (e.g., ceramic tile), cement, stone, painted surfaces (e.g., automobile body panels, boat surfaces), metal (e.g., architectural columns), paper (e.g., adhesive release liners), cardboard (e.g., food containers), thermosets, thermoplastics (e.g., polycarbonate, acrylics, polyolefins, polyurethanes, polyesters, polyamides, polyimides, phenolic resins, cellulose diacetate, cellulose triacetate, polystyrene, and styrene-acrylonitrile copolymers), and combinations thereof. The substrate may be a film, sheet, or it may have some other form. The substrate may comprise a transparent or translucent display element, optionally having a ceramer hardcoat thereon.

In some embodiments, a coating composition comprising a mixture of the fluorochemical urethane compounds and a solvent is provided. The coating compositions of the present invention comprise solvent suspensions, dispersions or solutions of the fluorochemical compounds of the present invention. When applied as coatings, the coating compositions impart oil- and water-repellency properties, and/or stain-release and stain-resistance characteristics to any of a wide variety of substrates.

The fluorochemical compounds can be dissolved, suspended, or dispersed in a variety of solvents to form coating compositions suitable for use in coating onto a substrate. Generally, the solvent solutions can contain from about 0.1 to about 50 percent, or even up to about 90 percent, by weight non-volatile solids (based on the total weight of the solid components). Coating compositions preferably contain from about 0.1 to about 10 weight percent fluorochemical urethane compounds, based on the total solids. Preferably the amount of fluorochemical urethane compounds used in the coating is about 0.1 to about 5 weight percent, most preferably from about 0.2 to about 1 weight percent, of the total solids. Suitable solvents include alcohols, esters, glycol ethers, amides, ketones, hydrocarbons, hydrofluorocarbons, hydrofluoroethers, chlorohydrocarbons, chlorocarbons, and mixtures thereof.

For ease of manufacturing and for reasons of cost, the compositions of the present invention can be prepared shortly before use by diluting a concentrate of one or more of the compounds of Formula I. The concentrate will generally comprise a concentrated solution of the fluorochemical urethane in an organic solvent. The concentrate should be stable for several weeks, preferably at least 1 month, more preferably at least 3 months. It has been found that the compounds can be readily dissolved in an organic solvent at high concentrations.

The coating compositions of this invention optionally contain silsesquioxanes. The silsesquioxanes may be blended with the coating composition, or alternatively and coating of the compounds of Formula I may be coated on a previously applied coating of the silsesquioxanes. Useful silsesquioxanes include co-condensates of diorganooxysilanes (or hydrosylates thereof) of the formula $R^{10}_2Si(OR^{11})_2$ with organosilanes (or hydrosylates thereof) of the formula $R^{10}_2SiO_{312}$ where each $R^1_2$ is an alkyl group of 1 to 6 carbon atoms or an aryl group and $R^{11}$ represents an alkyl radical with 1 to 4 carbon atoms. Preferred silsesquioxanes are neutral or anionic silsesquioxanes, prior to addition to the composition. Useful silsesquioxanes can be made by the techniques described in U.S. Pat. Nos. 3,493,424 (Mohrlok et al.), 4,351,736 (Steinberger et al.), 5,073,442 (Knowlton et al.) 4,781,844 (Kortmann, et al), and 4,781,844. Silsesquioxanes may be added in amounts of 90 to 99.9 wt. % relative to the total solids.

The silsesquioxanes may be prepared by adding silanes to a mixture of water, a buffer, a surface active agent and optionally an organic solvent, while agitating the mixture under acidic or basic conditions. It is preferable to add the quantity of silane uniformly and slowly in order to achieve a narrow particle size of 200 to 500 Angstroms. The exact amount of silane that can be added depends on the substituent R and whether an anionic or cationic surface-active agent is used. Co-condensates of the silsesquioxanes in which the units can be present in block or random distribution are formed by the simultaneous hydrolysis of the silanes. The amount of tetraorganosilanes, including tetralkoxysilanes and hydrosylates thereof (e.g. of the formula $Si(OH)_4$) present is less than 10 wt. %, preferably less than 5 wt. %, more preferably less than 2 wt. % relative to the weight of the silsesquioxane.

The following silanes are useful in preparing the silsesquioxanes of the present invention: methyltrimethoxysilane, methyltriethoxysilane, methyltriisopropoxyoxysilane, ethyltrimethoxysilane, ethyltriethoxysilane, propyltrimethoxysilane, isobutyltrimethoxysilane, isobutyltriethoxysilane, 2-ethylbutyltriethoxysilane, and 2-ethylbutoxytriethoxysilane.

The composition may be applied to the substrate by conventional techniques such as, for example, spraying, knife coating, notch coating, reverse roll coating, gravure coating, dip coating, bar coating, flood coating, dip coating or spin coating. The composition may be applied to any thickness to provide the desired level of water, oil, stain, and soil repellency. Typically, the composition is applied to the substrate as a relatively thin layer resulting in a dried cured layer having a thickness in a range of from about 40 nm to about 60 nm, although thinner and thicker (e.g., having a thickness up to 100 micrometers or more) layers may also be used. Next, any optional solvent is typically at least partially removed (e.g., using a forced air oven), and the composition is then at least partially cured to form a durable coating.

A preferred coating method for application of a fluorochemical urethane silane of the present invention includes dip coating. A substrate to be coated can typically be contacted with the treating composition at room temperature (typically, about 20 to about 25° C.). Alternatively, the mixture can be applied to substrates that are preheated at a temperature of for example between 60 and 150° C. This is of particular interest for industrial production, where e.g. ceramic tiles can be treated immediately after the baking oven at the end of the production line. Following application, the treated substrate can be dried and cured at ambient or elevated temperature, e.g. at 40 to 300° C. and for a time sufficient to dry. The process may also require a polishing step to remove excess material.

The present invention provides a protective coating on substrate that is relatively durable, and more resistant to contamination and easier to clean than the substrate surface itself. The present invention provides in one embodiment a method and composition for use in preparing a coated article comprising a substrate, preferably a hard substrate, and an anti-soiling coating of greater than a monolayer (which is typically greater than about 15 Angstroms thick deposited thereon. Preferably an antisoiling coating of the present invention is at least about 20 Angstroms thick, and more preferably, at least about 30 Angstroms thick. Generally, the thickness of the coating is less than 10 micrometers, preferably less than 5 micrometers. The coating material is typically present in an amount that does not substantially change the appearance and optical characteristics of the article.

EXAMPLES

Objects and advantages of this invention are further illustrated by the following examples, but the particular materials and amounts thereof recited in these examples, as well as other conditions and details, should not be construed to unduly limit this invention. These examples are merely for illustrative purposes only and are not meant to be limiting on the scope of the appended claims.

All parts, percentages, ratios, etc. in the examples and the rest of the specification are by weight, unless noted otherwise. Solvents and other reagents used were obtained from Aldrich Chemical Company, Milwaukee, Wis. unless otherwise noted.

Test Methods

Nuclear Magnetic Resonance (NMR)

$^1H$ and $^{19}F$ NMR spectra were run on a Varian UNITYplus 400 Fourier transform NMR spectrometer (available from Varian NMR Instruments, Palo Alto, Calif.).

IR Spectroscopy (IR)

IR spectra were run on a Thermo-Nicolet, Avatar 370 FTIR, obtainable from Thermo Electron Corporation, Waltham, Mass.

Method for Forming Coatings on Polycarbonate Plaques

Polycarbonate plaques (10 cm by 10 cm) were coated with coating compositions comprising fluorochemical urethane compositions according to this invention using the dip coating process. To form the coatings, each polycarbonate plaque was first immersed into a SHP 401 primer at a rate of 90 cm per minute rate. Once the entire plaque was immersed in the primer, the plaque was removed from the primer a rate of 90 cm per minute rate and was allowed to air dry at room temperature for 10 minutes. The dried plaque was then immersed into a solution of SHC-1200 or a solution of SHC-1200 containing 0.3 weight percent of a fluorochemical urethane silane prepared according to this invention. The plaque was immersed in to the coating solution at a rate of 90 cm per minute and withdrawn out at 19 cm per minute, air dried at room temperature for 20 minutes and finally heated in an oven for 30 minutes at 130° C.

Ink Repellency Test

This test was used to measure the ink repellency of the coatings on polycarbonate plaques. Coated polycarbonate plaques were prepared as described above. A line was drawn across the surface of a coated polycarbonate plaque using a Sharpie™ Fine Point, Series 30000 permanent marker (available from Sanford, a division of Newell Rubbermaid) The samples were rated for appearance and for the ability to repel a black Sharpie marker.

| Ink Repellency Test Ratings | |
|---|---|
| Ranking | Description |
| 1 | Ink beaded well |
| 2 | Some beading |
| 3 | Little beading |
| 4 | No beading |

Ink Repellency Durability Test

To measure the durability of ink repellency of coated polycarbonate plaques a modified Oscillating Sand Method (ASTM F 735-94) was used. A coated polycarbonate plaque (i.e., test sample prepared as described above) was secured using vinyl tape and rubber bands onto a jar, with an 87 mm inner diameter (VWR 36318-860, commercially available from VWR Bristol, Conn.), containing 50 grams of unused 20-30 mesh Ottawa sand (obtained from VWR, Bristol, Conn.). The jar was placed in a shaker (VWR DS-500E, obtained from VWR Bristol, Conn.) with the side containing the test sample at the bottom and the shaker was operated oscillating at a rate of 225 rpm for 10 minutes. At the end of ten minutes, the polycarbonate plaque was removed and a Sharpie permanent marker was used to draw a line across its surface that was in contact with the sand. The normalized (%) length of the 87 mm ink line that did not bead up was measured and reported as percent ink repellency loss. The data reported is the average of three independent tests. Lower numbers indicate better performance.

Taber Haze Test

This test was run on polycarbonate plaques coated as described above. The test procedure was that of Procedure No CET-APRS-STP-0316, Revision 1.1, dated 24 Oct. 2005 by National Institute of Occupational Safety and Health. A number less than 4 is desired.

Steel Wool Durability Test

The abrasion resistance of the coated and cured polycarbonate plaques (prepared as described above) were tested cross-web to the coating direction by use of a mechanical device capable of oscillating a steel wool sheet adhered to a stylus across the film's surface. The stylus oscillated over a 90 mm wide sweep width at a rate of 315 mm/sec (3.5 wipes/sec) wherein a "wipe" is defined as a single travel of 90 mm. The stylus had a flat, cylindrical base geometry with a diameter of 3.2 cm. The stylus was designed to enable attachment of additional weights to increase the force exerted by the steel wool normal to the film's surface. The samples were tested at a 500 g load for 25 wipes. The #0000 steel wool sheets were "Magic Sand-Sanding Sheets" available from Hut Products, Fulton, Mo. The #0000 has a specified grit equivalency of 600-1200 grit sandpaper. The 3.2 cm steel wool discs were die cut from the sanding sheets and adhered to the 3.2 cm stylus base with 3M Brand Scotch Permanent Adhesive Transfer tape. The contact angles were measured on the wear track after the steel wool abrasion, and on an area of the plaque adjacent to the wear track that was not effected by the steel wool track (i.e., before steel wool testing). The contact angle measurements were made using the "method for Measuring Contact Angles" as described below. The reported data represents the average of measurements done on three plaques. Three drops were placed on each plaque, with contact angle measured on the right and the left sides of each of the drops.

Method for Measuring Contact Angles

The coated polycarbonate plaques (prepared as described above) were treated with IPA, which was allowed to evaporate, before being subjected to measurement of water contact angles. Measurements were made using as-received reagent-grade hexadecane and de-ionized water filtered through a filtration system (obtained from Millipore Corporation Billerica, Mass.), on a video contact angle analyzer (available as product number VCA-2500XE from AST Products Billerica, Mass.). Reported values are the averages of measurements on at least three drops measured on the right and the left sides of the drops. Drop volumes were 5 μL for static measurements.

Solvent Resistance Test

Four chambers were filled with a different solvent: ethanol, isopropanol, toluene and MEK. Each plaque prepared as described above was placed in all four chambers for 60 seconds. Observations such as de-lamination, cracks, discoloration, and any other changes in the coating were recorded. Each plaque was then placed in the solvent chambers for an additional 300 seconds. All observations were again recorded.

Materials

Hexamethylene diisocyanate (Desmodur™ N100) was obtained from Bayer Polymers LLC of Pittsburgh, Pa.

HFPO—C(O)N(H)CH$_2$CH$_2$OH was prepared by a procedure similar to that described in U.S. Publication No. 2004-0077775, entitled "Fluorochemical Composition Comprising a Fluorochemical Polymer and Treatment of a Fibrous Substrate Therewith".

Pentaerythritol Triaclate PET$_3$A was obtained from Sartomer Company of Warrington, Pa. under trade name SR444C.

Poly(methyl methacrylate) Primer (SHP™ 401) was obtained from GE Silicones of Waterford, N.Y.

Methylsilsesquioxane solution (SHC™ 1200) was obtained from GE Silicones of Waterford, N.Y.

N-methyl Aminopropyltrimethoxy silane (MAPTMS) was obtained from Union Carbide Chemicals and Plastics Co. of Danbury, Conn.

Bis(propyl-3-trimethoxysilane) amine was obtained from Gelest, Morrisville, Pa.

Aminopropyltrimethoxy silane, (APTMS), was obtained from Sigma-Aldrich, Milwaukee, Wis.

Hydroxyethyl acrylate (HEA) was obtained from Sigma-Aldrich, Milwaukee, Wis. Dibutyltin dilaurate (DBTDL) was obtained from Sigma-Aldrich, Milwaukee, Wis.

Polycarbonate Plaques were molded by Minnesota Mold & Engineering, Vadnais Heights, Minn. (from GE Lexan™ 101, Mount Vernon, Ind.).

Example 1 a) Preparation of [DESN100/0.15 HFPOC(O)N(H)CH$_2$CH$_2$OH/0.90 HEA] Intermediate A 200 mL round bottom flask equipped with stirring bar was charged with 12.5 g (0.0654 eq, 1.0 mole fraction, 191.0 isocyanate equivalent weight) DESN100, 1.6 mg (50 ppm with respect to solids) DBTDL, 0.05 g BHT, and 32.24 g THF to form a mixture. The flask was placed in a 55° C. bath and 12.90 g (0.0098 eq, 0.15 mole fraction, 1314 molecular weight) HFPOC(O)N(H)CH$_2$CH$_2$OH was added to the mixture over 10 minutes via a pressure equalizing dropping funnel. Two hours after the addition was complete, 6.84 g (0.0589 eq, 0.85 mole fraction) hydroxyethyl acrylate was added and the mixture was allowed to react overnight. After reaction overnight, the IR spectrum of a sample had no peaks corresponding to a NCO group at 2265 cm$^{-1}$. The reaction product was diluted by addition of 5.48 g of THF to adjust its composition to 50% solids.

b) Preparation of Perfluoropolyether Urethane Silane 5 g (0.004565 moles of acrylate functionality) of intermediate prepared above in a) was charged in a 25 ml round bottom flask equipped with magnetic stirring bar. The flask was placed in an oil bath and the content of the flask were placed under nitrogen atmosphere. 1.56 g (0.004565 moles) of bis(trimethoxysilylpropyl)amine was added into the flask dropwise at room temperature. The reaction mixture was stirred at room temperature for 15 minutes and then heated to 55° C. for 4 hours. The completion of reaction was determined by the disappearance of acrylate peaks in $^1$H NMR spectrum. The product was stored under nitrogen atmosphere in amber colored bottles in a refrigerator prior to coating.

Example 2 a) Preparation of [DESN100/0.30 HFPOC(O)N(H)CH$_2$CH$_2$OH/0.75 HEA] Intermediate A 200 mL round bottom flask equipped with stirring bar was charged with 12.5 g (0.0654 eq, 1.0 mole fraction) DESN100, 1.6 mg DBTDL, 0.05 g BHT, and 44.0 g THF to form a mixture. The flask was placed in a 55° C. bath and 25.80 g (0.0196 eq, 0.30 mole fraction, 1314 molecular weight) HFPOC(O)N(H)CH$_2$CH$_2$OH was added to the mixture over 10 minutes via a pressure equalizing dropping funnel. Two hours after the addition was complete, 5.70 g (0.0491 eq, 0.75 mole fraction) hydroxyethyl acrylate was added and the mixture was allowed to react overnight. After reaction overnight, the IR spectrum of a sample had no peaks corresponding to a NCO group at 2265 cm$^{-1}$. The reaction product was diluted by addition of 11.44 g of THF to adjust its composition to 50% solids.

b) Preparation of Perfluoropolyether Urethane Silane 5 g (0.00278 moles of acrylate functionality) of intermediate prepared above in a) was charged in a 25 ml round bottom flask equipped with magnetic stirring bar. The flask was placed in an oil bath and the content of the flask were place under nitrogen atmosphere. 0.9493 g (0.00278 moles) of bis(trimethoxysilylpropyl)amine was added into the flask dropwise at room temperature. The reaction mixture was stirred at room temperature for 15 minutes and heated to 55° C. for 4 hours. The completion of reaction was determined by the disappearance of acrylate peaks in $^1$H NMR spectrum. The product was stored under nitrogen atmosphere in amber colored bottles in a refrigerator prior to coating.

Example 3 a) Preparation of [DESN100/0.50 HFPOC(O)N(H)CH$_2$CH$_2$OH/0.55 HEA] Intermediate A 200 mL round bottom flask equipped with stirring bar was charged with 12.5 g (0.0654 eq, 1.0 mole fraction) DESN100, 1.6 mg DBTDL, 0.05 g BHT, and 59.88 g THF to form a mixture. The flask was placed in a 55° C. bath and 43.0 g (0.0327 eq, 0.50 mole fraction, 1314 molecular weight) HFPOC(O)N(H)CH$_2$CH$_2$OH was added to the mixture over 10 minutes via a pressure equalizing dropping funnel. Two hours after the addition was complete, 4.18 g (0.0360 eq, 0.55 mole fraction) hydroxyethyl acrylate was added and the mixture was allowed to react overnight. After reaction overnight, the IR spectrum of a sample had no peaks corresponding to a NCO group at 2265 cm$^{-1}$. The reaction product was diluted by addition of 29.62 of THF to adjust its composition to 50% solids.

b) Preparation of Perfluoropolyether Urethane Silane 5 g (0.0015 moles of acrylate functionality) of intermediate prepared above in a) was charged in a 25 ml round bottom flask equipped with magnetic stirring bar. The flask was placed in an oil bath and the content of the flask were place under nitrogen atmosphere. 0.5138 g (0.0015 moles) of bis(trimethoxysilylpropyl)amine was added into the flask drop wise at room temperature. The reaction mixture was stirred at room temperature for 15 minutes and heated to 55° C. for 4 hours. The completion of reaction was determined by the disappearance of acrylate peaks in $^1$H NMR spectrum. The product was stored under nitrogen atmosphere in amber colored bottles in a refrigerator prior to coating.

Example 4 a) Preparation of [DESN100/75% HEA/15% PET$_3$A/15% HFPOC(O)NHCH$_2$CH$_2$OH] Intermediate A 200 mL round bottom flask equipped with stirring bar was charged with 12.5 g (0.0654 eq, 1.0 mole fraction) DESN100, 1.6 mg DBTDL, 0.05 g BHT, and 35.24 g THF to form a mixture. The flask was placed in a 55° C. bath and 12.9 g (0.0098 eq, 0.15 mole fraction, 1314 molecular weight) HFPOC(O)N(H)CH$_2$CH$_2$OH was added to the mixture over 10 minutes via a pressure equalizing dropping funnel. Two hours after the addition was complete, 4.13 g (0.0098 eq, 0.15 mole fraction) PET$_3$A was added to the mixture. Two hours after the addition was complete, 5.70 g (0.0491 eq, 0.75 mole fraction) hydroxyethyl acrylate was added and the mixture was allowed to react overnight. After reaction overnight, the IR spectrum of a sample had no peaks corresponding to a NCO group at 2265 cm$^{-1}$. The reaction product was diluted by addition of 5.48 g of THF to adjust its composition to 50% solids.

b) Preparation of Perfluoropolyether Urethane Silane 35.24 g (0.046*moles of acrylate functionality) of intermediate prepared above in a) was charged in a 100 ml round bottom flask equipped with magnetic stirring bar. The flask was placed in an oil bath and the content of the flask were place under nitrogen atmosphere. 15.77 g (1.417 eq, 0.046 mole fraction) of bis(trimethoxysilylpropyl)amine was added into the flask drop wise at room temperature. The reaction mixture was stirred at room temperature for 15 minutes and heated to 55° C. for 4 hours. The completion of reaction was determined by the disappearance of acrylate peaks in $^1$H NMR spectrum. The product was stored under nitrogen atmosphere in amber colored bottles in a refrigerator prior to coating.

The number of equivalents of bis(trimethoxysilylpropyl) amine used was determined by first assuming that PET$_3$A of 420.94 OH equivalent weight used was 70% Pentaerythritol Triacrylate (298/421.4) and 30% Pentaerythritol Tetraacrylate. Next, the number of acrylate moieties present per mole of OH equivalent was determined by calculating the following equation: [the sum for all components of (number of acrylate moieties present in component)(hydroxyl equivalent weight of the total species)(component's fraction of the total species)]/molecular weight of component. For example, Pentaerythritol Triacrylate's values in the equation are: [(3)*(420.94)*(0.7)/(298)]+[(4)*(420.94)*(0.3)/352]=4.40. Thus the number of equivalents of acrylate from the PET$_3$A and HEA in preparation 5a) was (0.0098*4.40)+(0.0491)=0.0922. Since half of the solution was used for preparation 5b), the number of moles of acrylate in the reaction is 0.046. Similar calculations were made for examples 6, 7, and 8.

Example 5

Preparation of Perfluoropolyether Urethane Silane 35.24 g (0.046 moles of acrylate functionality) of intermediate prepared as described above in Example 4a) was charged in a 100 ml round bottom flask equipped with magnetic stirring bar. The flask was placed in an oil bath and the content of the flask were placed under nitrogen atmosphere. 8.92 g (0.046 eq*, 1.417 fraction) of MAPTMS was added into the flask dropwise at room temperature. The reaction mixture was stirred at room temperature for 15 minutes and heated to 55° C. for 4 hours. The completion of reaction was determined by the disappearance of acrylate peaks in $^1$H NMR spectrum. The product was stored under nitrogen atmosphere in amber colored bottles in a refrigerator prior to coating.

Example 6 a) Preparation of [DESN100/60% HEA/30% PET$_3$A/15% HFPOC(O)NHCH$_2$CH$_2$OH] Intermediate A 200 mL round bottom flask equipped with stirring bar was charged with 12.5 g (0.0654 eq, 1.0 mole fraction) DESN100, 1.6 mg DBTDL, 0.05 g BHT, and 35.24 g THF to form a mixture. The flask was placed in a 55° C. bath and 12.9 g (0.0098 eq, 0.15 mole fraction, 1314 molecular weight) HFPOC(O)N(H)CH$_2$CH$_2$OH was added to the mixture over 10 minutes via a pressure equalizing dropping funnel. Two hours after the addition was complete, 8.26 (0.0196 eq, 0.30 mole fraction) PET$_3$A was added to the mixture. Two hours after the addition was complete, 4.56 g (0.0393 eq, 0.6 mole fraction) hydroxyethyl acrylate was added and the mixture was allowed to react overnight. After reaction overnight, the IR spectrum of a sample had no peaks corresponding to a NCO group at 2265 cm$^{-1}$. The reaction product was diluted by addition of 5.48 g of THF to adjust its composition to 50% solids.

b) Preparation of Perfluoropolyether Urethane Silane 38.23 g (0.063 moles of acrylate functionality) of intermediate prepared above in a) was charged in a 100 ml round bottom flask equipped with magnetic stirring bar. The flask was placed in an oil bath and the content of the flask were place under nitrogen atmosphere. 21.49 g (0.063 eq, 1.927 mole fraction) of bis(trimethoxysilylpropyl)amine was added into the flask drop wise at room temperature. The reaction mixture was stirred at room temperature for 15 minutes and heated to 55° C. for 4 hours. The completion of reaction was determined by the disappearance of acrylate peaks in $^1$H NMR spectrum. The product was stored under nitrogen atmosphere in amber colored bottles in a refrigerator prior to coating.

Example 7

Preparation of Perfluoropolyether Urethane Silane 38.23 g (0.063 moles of acrylate functionality) of intermediate prepared as described above in Example 6a) was charged in a 100 ml round bottom flask equipped with magnetic stirring bar. The flask was placed in an oil bath and the content of the flask were place under nitrogen atmosphere. 12.16 g (0.63 eq, 1.927 mole fraction) of MAPTMS was added into the flask drop wise at room temperature. The reaction mixture was stirred at room temperature for 15 minutes and heated to 55° C. for 4 hours. The completion of reaction was determined by the disappearance of acrylate peaks in $^1$H NMR spectrum. The product was stored under nitrogen atmosphere in amber colored bottles in a refrigerator prior to coating.

Example 1-7 materials were used to prepare coatings on polycarbonate plaques according to the "Method for Forming Coatings on Polycarbonate Plaques" described above. The performance of the resulting coatings were then evaluated using Taber Haze Change, Ink Repellency Test, Ink Repellency Durability Test, Steel Wool Test and Solvent Test as described above.

Table 1 below summarizes the results of Taber Haze Test, Ink Repellency Test and Ink Repellency Durability Test for coatings made using SHC-1200 with no added fluorochemical urethane silane and Example 1-7 materials.

TABLE 1

| Example | Taber Haze Test | Ink Repellency Test | Ink Repellency Durability Test, % |
|---|---|---|---|
| SHC-1200 control | 3.57 | 4 | 100 |
| 1 | 3.48 | 1 | 7 |
| 2 | 3.05 | 2 | 70 |
| 3 | 3.47 | 1 | 97 |
| 4 | 3.06 | 1 | 94 |
| 5 | 2.49 | 1 | 94 |
| 6 | 2.97 | 1 | 100 |
| 7 | 3.12 | 1 | 100 |

Table 2 below summarizes the results of Steel Wool Test for coatings made using SHC-1200 with no added fluorochemical urethane silane and Example 1-7 materials.

TABLE 2

| | Before Steel Wool Test | | After Steel Wool Test | |
|---|---|---|---|---|
| Example | Contact Angle | Standard Deviation | Contact Angle | Standard Deviation |
| SHC-1200 control | 94.1 | 1.3 | 87.6 | 1.9 |
| 1 | 107.1 | 0.9 | 105.5 | 1.7 |
| 2 | 104.9 | 0.7 | 103 | 1.4 |
| 3 | 96.5 | 1.1 | 93.7 | 2.3 |
| 4 | 100.3 | 0.5 | 98.3 | 0.7 |
| 5 | 100.4 | 0.5 | 97.7 | 1 |
| 6 | 97.4 | 0.5 | 93 | 0.9 |
| 7 | 97.7 | 0.9 | 92.5 | 1.4 |

Table 3 below summarizes the results of Solvent Test for coatings made using SHC-1200 with no added fluorochemical urethane silane and Example 1-3 materials.

TABLE 3

| Example | Solvent | After 60 seconds | After 300 seconds |
|---|---|---|---|
| SHC-1200 control | Ethanol | No effect | No effect |
| SHC-1200 control | Isopropanol | No effect | No effect |
| SHC-1200 control | Toluene | No effect | No effect |
| SHC-1200 control | MEK | No effect | Few tiny cracks by edges |
| 1 | Ethanol | No effect | No effect |
| 1 | Isopropanol | No effect | No effect |
| 1 | Toluene | No effect | Few tiny cracks |
| 1 | MEK | White spots and long thin cracks | Cracks and some white spots, de-lamination by edges |
| 2 | Ethanol | No effect | No effect |
| 2 | Isopropanol | No effect | No effect |
| 2 | Toluene | No effect | Few tiny cracks |
| 2 | MEK | No effect | Long and thin cracks all over coating |
| 3 | Ethanol | No effect | No effect |
| 3 | Isopropanol | No effect | No effect |
| 3 | Toluene | No effect | Few tiny cracks |
| 3 | MEK | No effect | Few tiny cracks, de-lamination by edges |

The invention claimed is:

1. A compound of the formula

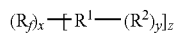

wherein
- $R_f$ is a fluorine-containing group,
- $R^1$ is the residue of a polyisocyanate,
- $R^2$ is a silane-containing moiety derived from the Michael reaction between a nucleophilic acryloyl compound and an aminosilane,
- x and y are each independently at least 1, and z is 1 or 2.

2. The composition of claim 1 wherein $R^2$ is of the formula:

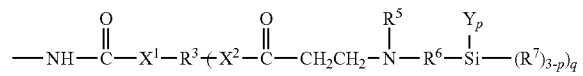

wherein
- $X^1$ is —O— or —S—,
- $X^2$ is —O—, —S— or —NR$^4$—, where $R^4$ is H or $C_1$-$C_4$ alkyl,
- $R^3$ is a polyvalent alkylene or arylene groups, or combinations thereof, said alkylene groups optionally containing one or more catenary oxygen atoms;
- $R^5$ is $C_1$-$C_4$ alkyl, or —R$^6$—Si(Y$_p$)(R$^7$)$_{3-p}$;
- $R^6$ is a divalent alkylene group, said alkylene groups optionally containing one or more catenary oxygen atoms;
- Y is a hydrolysable group,
- $R^7$ is a monovalent alkyl or aryl group,
- p is 1, 2 or 3, preferably 3, and
- q is 1 to 5.

3. The compounds of claim 1 wherein $R_f$ comprises a fluorine-containing groups selected from monovalent perfluoroalkyl and perfluorooxyalkyl groups, and divalent perfluoroalkylene and perfluorooxyalkylene groups.

4. The compound of claim 1, where $R_f$ is of the formula:

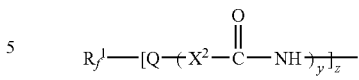

wherein
- $R_f^1$ is a monovalent perfluoroalkyl or a perfluorooxyalkyl group, or a divalent perfluoroalkylene or a perfluorooxyalkylene group,
- Q is a covalent bond, or a polyvalent alkylene group of valency z, said alkylene optionally containing one or more catenary oxygen atoms,
- $X^2$ is —O—, —NR$^4$— or S—, where $R^4$ is H or $C_1$-$C_4$ alkyl,
- z is 1 or 2.

5. The compound of claim 4 wherein $R_f^1$ is a monovalent perfluorooxyalkyl group, or a divalent a perfluorooxyalkylene group comprising one or more perfluorinated repeating units selected from the group consisting of —(CF$_2$F$_{2n}$O)—, —(CF(Z)O)—, —(CF(Z)CF$_2$F$_{2n}$O)—, —(C$_n$F$_{2n}$CF(Z)O)—, —(CF$_2$CF(Z)O)—, and combinations thereof, wherein n is 1 to 4 and Z is a perfluoroalkyl group, a perfluoroalkoxy group, or perfluorooxyalkyl group.

6. The compounds of claim 4 wherein $R_f^1$ comprises a group of the formula

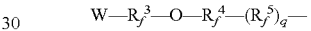

wherein
- W is F for monovalent perfluorooxyalkyl, and an open valence ("-") for divalent perfluorooxyalkylene;
- $R_f^3$ represents a perfluoroalkylene group,
- $R_f^4$ represents a perfluoroalkyleneoxy group consisting of perfluorooxyalkylene groups having 1, 2, 3 or 4 carbon atoms or a mixture of such perfluorooxyalkylene groups,
- $R_f^5$ represents a perfluoroalkylene group, and
- q is 0 or 1.

7. The compound of claim 3 wherein said perfluorooxyalkylene group is selected from one or more of —[CF$_2$—CF$_2$—O]$_r$—; —[CF(CF$_3$)—CF$_2$—O]$_s$—; —[CF$_2$CF$_2$—O]$_r$—[CF$_2$O]$_t$—, —[CF$_2$CF$_2$CF$_2$CF$_2$-o]$_u$- and —[CF$_2$—CF$_2$—O]$_r$—[CF(CF$_3$)—CF$_2$—O]$_s$—; wherein each of r, s, t and u each are integers of 1 to 50.

8. The compounds of claim 1 wherein $R_f$ comprises a monovalent perfluorooxyalkylene group and z is 1.

9. The compounds of claim 1 wherein $R_f$ is derived from a fluorinated polyol.

10. The compound of claim 2, wherein Y is a halogen, a $C_1$-$C_4$ alkoxy group, or a $C_1$-$C_4$ acyloxy group.

11. The compound of claim 4 wherein $R_f^1$ is a monovalent perfluorooxyalkyl group and z is 1.

12. The compounds of claim 2 wherein the molar ratio of silane groups to —NH—C(O)—X$^1$— groups is greater than 1:1.

13. The compound of claim 2 derived from a nucleophilic acryloyl compound is of the formula

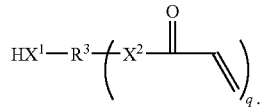

where
X¹ is —O— or —S—,
X² is —O—, —S— or —NR⁴—, where R⁴ is H or $C_1$-$C_4$ alkyl,
R³ is a divalent alkylene or arylene groups, or combinations thereof, said alkylene groups optionally containing one or more catenary oxygen atoms; and q is 1 to 5.

14. The compounds of claim 2, derived from an aminosilane is of the formula:

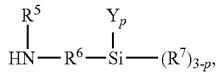

wherein
R⁵ is H, $C_1$-$C_4$ alkyl, or —R⁶—Si($Y_p$)($R^7$)$_{3-p}$;
R⁶ is a divalent alkylene group, said alkylene groups optionally containing one or more catenary oxygen atoms;
Y is a hydrolysable group,
R⁷ is a monovalent alkyl or aryl group,
p is 1, 2 or 3, preferably 3.

15. A coating composition comprising at least one compound of claim 1 and a solvent.

16. The coating composition of claim 15 further comprising a silsesquioxane.

17. A compound comprising the Michael addition reaction product of an aminosilane with a fluorine-containing urethane compound having pendent acrylate groups; said fluorine-containing urethane compound comprising the reaction product of a polyisocyanate, a nucleophilic fluorochemical compound, and a nucleophilic acryloyl compound.

18. The compound of claim 17 wherein said fluorine-containing urethane compound having pendent acrylate groups is of the formula:

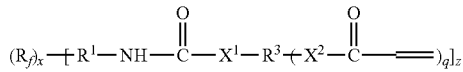

wherein
$R_f$ is a fluorine-containing group,
R¹ is the residue of a polyisocyanate,
X¹ is —O— or —S—,
X² is —O—, —S— or —NR⁴—, where R⁴ is H or $C_1$-$C_4$ alkyl,
R³ is a divalent alkylene or arylene groups, or combinations thereof, said alkylene groups optionally containing one or more catenary oxygen atoms;
z is 1 or 2, and
q is 1 to 5.

19. The compound of claim 17 wherein the aminosilane is of the formula

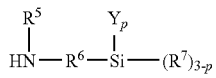

wherein
R⁵ is $C_1$-$C_4$ alkyl, or —R⁶—Si($Y_p$)($R^7$)$_{3-p}$;
R⁶ is a divalent alkylene group, said alkylene groups optionally containing one or more catenary oxygen atoms;
Y is a hydrolysable group,
R⁷ is a monovalent alkyl or aryl group,
p is 1, 2 or 3, preferably 3, and
q is 1 to 5.

* * * * *

UNITED STATES PATENT AND TRADEMARK OFFICE
CERTIFICATE OF CORRECTION

PATENT NO. : 7,825,272 B2
APPLICATION NO. : 12/445143
DATED : November 2, 2010
INVENTOR(S) : Suresh Subramaniya Iyer It is certified that error appears in the above-identified patent and that said Letters Patent is hereby corrected as shown below:

Column 1,
Line 30, after "clean" insert -- . --.

Column 3,
Line 50, delete "—[CF$_2$-CF$_2$O]$_r$," and insert -- —[CF$_2$-CF$_2$-O]$_r$ --.

Column 4,
Line 23, after "2" insert -- . --.

Column 6,
Line 15, delete "Desmodur™N-3600" and insert -- Desmodur™ N-3600 --.
Line 17, delete "Desmodure™" and insert -- Desmodur™ --.

Column 7,
Line 43, delete "—C$_n$F$_2$—)" and insert -- —C$_n$F$_{2n}$—) --.
Line 52, after "perfluorooxyalkylene" insert -- , --.

Column 8,
Line 15, delete "perfluoroxyalkylene" and insert -- perfluorooxyalkylene --.
Line 31, delete "C$_6$F$_{13}$SO$_2$N(CH)(CH$_2$)$_4$OH," and insert -- C$_6$F$_{13}$SO$_2$N(CH$_3$)(CH$_2$)$_4$OH, --.

Column 10,
Line 5, delete " 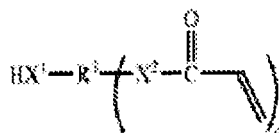 " and insert -- 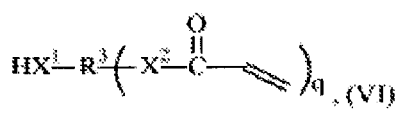 --.

Column 10,
Line 44, delete "diiacrylate)," and insert -- diacrylate), --.

Signed and Sealed this
Twenty-seventh Day of March, 2012

David J. Kappos
*Director of the United States Patent and Trademark Office*

Column 11,
Line 33, after "invention" insert -- . --.
Line 55, delete "α-aminopropyltripropoxysilane," and insert
-- α-aminopropyltripropoxysilane. --.

Column 14,
Line 58, delete "$R^{10}_2SiO_{312}$" and insert -- $R^{10}SiO_{3/2}$ --.
Line 58, delete "$R^1_2$" and insert -- $R^{10}$ --.
Line 65, delete "Silsequioxanes" and insert -- Silsesquioxanes --.

Column 18,
Line 20, delete "Triaclate PET$_3$A" and insert -- Triacrylate (PET$_3$A) --.

Column 18,
Lines 37-38, delete "Dibutyltin dilaurate (DBTDL) was obtained from Sigma-Aldrich, Milwaukee, Wis.".
Line 38, after "Wis.", insert -- Dibutyltin dilaurate (DBTDL) was obtained from Sigma-Aldrich, Milwaukee, Wis. --.

Column 20,
Line 58, before "The" insert -- * --.

Column 24,
Line 15, delete "or S—," and insert -- or —S—, --.
Line 23, delete "—(CF$_2$F$_{2n}$O)—," and insert -- —(C$_n$F$_{2n}$O)—, --.
Lines 60-65, Delete " " and insert -- 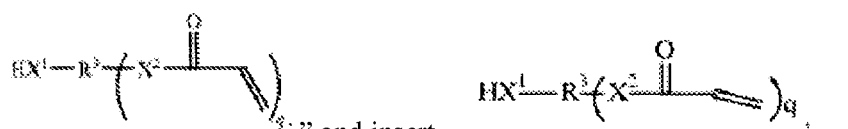 --.